United States Patent [19]

Stütz et al.

[11] 4,348,391
[45] Sep. 7, 1982

[54] SULFONAMIDO AND SULFAMOYLAMINO-ERGOLINE-I DERIVATIVES

[75] Inventors: Peter Stütz, Vienna, Austria; Theodor Fehr, Dornach; Paul Stadler, Biel-Benken, both of Switzerland

[73] Assignee: Sandoz Ltd., Basel, Switzerland

[21] Appl. No.: 189,068

[22] Filed: Sep. 22, 1980

Related U.S. Application Data

[63] Continuation of Ser. No. 973,158, Dec. 26, 1978, abandoned, which is a continuation-in-part of Ser. No. 896,703, Apr. 17, 1978, abandoned, which is a continuation of Ser. No. 752,070, Dec. 20, 1976, abandoned.

[30] Foreign Application Priority Data

Dec. 23, 1975 [CH] Switzerland ............... 16680/75
May 18, 1976 [CH] Switzerland ............... 6188/76

[51] Int. Cl.³ ............... C07D 457/12; A61K 31/48
[52] U.S. Cl. ............... 424/246; 424/248.5; 424/250; 424/261; 544/60; 544/125; 544/361; 546/67; 546/68
[58] Field of Search ............ 546/67, 68; 424/261, 424/250, 246, 248.5; 544/125, 361, 60

[56] References Cited

U.S. PATENT DOCUMENTS

| | | | |
|---|---|---|---|
| 2,533,698 | 12/1950 | Stoll et al. | 546/68 |
| 3,185,695 | 5/1965 | Bernardi et al. | 546/68 |
| 3,218,323 | 11/1965 | Hofmann et al. | 546/68 |
| 3,232,943 | 2/1966 | Hofmann et al. | 546/68 |
| 3,245,996 | 4/1966 | Hofmann et al. | 546/67 |
| 3,270,020 | 8/1966 | Hofmann et al. | 546/68 |
| 3,732,231 | 5/1973 | Semonsky et al. | 424/261 |
| 3,880,856 | 4/1975 | Bach et al. | 424/261 |
| 3,904,757 | 9/1975 | Slater | 424/261 |
| 3,920,664 | 11/1975 | Clemens et al. | 424/261 |
| 3,922,347 | 11/1975 | Bach et al. | 424/261 |
| 4,005,090 | 1/1977 | Semonsky et al. | 424/261 |

FOREIGN PATENT DOCUMENTS

| | | | |
|---|---|---|---|
| 831488 | 1/1976 | Belgium. | |
| 2874M | 9/1963 | France | 546/68 |
| 1041862 | 9/1966 | United Kingdom | 546/68 |

OTHER PUBLICATIONS

Clemens et al.; Endocrinology, vol. 94, p. 1171 (1974).

Primary Examiner—Mary C. Lee
Attorney, Agent, or Firm—Gerald D. Sharkin; Robert S. Honor; Thomas O. McGovern

[57] ABSTRACT

The present invention provides compounds of formula I,

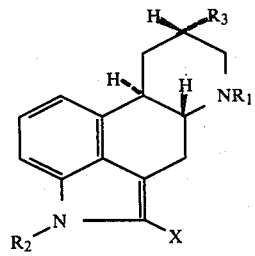

wherein
X is hydrogen, chlorine or bromine,
$R_1$ is methyl or ethyl,
$R_2$ is alkyl of 1 to 4 carbon atoms or allyl,
$R_3$ is $CH_2CN$ or a group $-NR_4R_5$, wherein $R_4$ is hydrogen or alkyl of 1 to 4 carbon atoms, and $R_5$ is alkanoyl of 1 to 5 carbon atoms, alkoxycarbonyl of 2 to 5 carbon atoms in the aggregate thereof, or mono-, di- or tri-haloalkoxycarbonyl of 3 to 5 carbon atoms, wherein the alkoxy group is substituted by halogen other than in the α position to the oxygen atom, or $R_5$ is $SO_2R_6$, wherein $R_6$ is alkyl of 1 to 4 carbon atoms, mono-, di- or tri-haloalkyl of 1 to 4 carbon atoms, phenyl, phenyl mono-substituted by halogen or alkoxy of 1 to 4 carbon atoms, or pyridyl, or $R_6$ is a group $NR_7R_8$, wherein $R_7$ and $R_8$ are, independently, hydrogen or alkyl of 1 to 4 carbon atoms, or $R_7$ and $R_8$ together form $-[CH_2]_n-$ or $-[CH_2]_2-A-[CH_2]_2-$, wherein n is a whole number from 3 to 7, and A is oxygen, sulphur, or nitrogen substituted by alkyl of 1 to 4 carbon atoms or phenyl which are useful as prolactin inhibitors, anti-parkinson agents, and anti-depressants.

12 Claims, No Drawings

SULFONAMIDO AND SULFAMOYLAMINO-ERGOLINE-I DERIVATIVES

This is a continuation of application Ser. No. 973,158, filed Dec. 26, 1978, now abandoned, which in turn is a continuation-in-part of application Ser. No. 896,703, filed Apr. 17, 1978, now abandoned, which in turn is a continuation of application Ser. No. 752,070, filed Dec. 20, 1976, now abandoned.

The present invention relates to ergoline derivatives.

The present invention provides compounds of formula I,

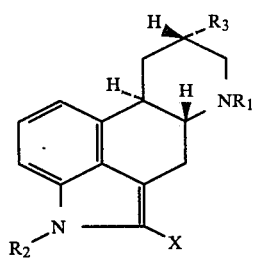

wherein
X is hydrogen, chlorine or bromine,
$R_1$ is methyl or ethyl,
$R_2$ is alkyl of 1 to 4 carbon atoms or allyl,
$R_3$ is $CH_2CN$ or a group $-NR_4R_5$, wherein $R_4$ is hydrogen or alkyl of 1 to 4 carbon atoms, and $R_5$ is alkanoyl of 1 to 5 carbon atoms, alkoxycarbonyl of 2 to 5 carbon atoms in the aggregate thereof, or mono-, di- or tri-haloalkoxycarbonyl of 3 to 5 carbon atoms, wherein the alkoxy group is substituted by halogen other than in the α position to the oxygen atom, or $R_5$ is $SO_2R_6$, wherein $R_6$ is alkyl of 1 to 4 carbon atoms, mono-, di- or tri-haloalkyl of 1 to 4 carbon atoms, phenyl, phenyl mono-substituted by halogen or alkoxy of 1 to 4 carbon atoms, or pyridyl, or $R_6$ is a group $NR_7R_8$, wherein $R_7$ and $R_8$ are, independently, hydrogen or alkyl of 1 to 4 carbon atoms, or $R_7$ and $R_8$ together form $-[CH_2]_n-$ or $-[CH_2]_2-A-[CH_2]_2-$, wherein n is a whole number from 3 to 7, and A is oxygen, sulphur, or nitrogen substituted by alkyl of 1 to 4 carbon atoms or phenyl.

X is preferably hydrogen.

Except where otherwise stated alkyl and alkoxy have preferably 2, especially, 1 carbon atom.

$R_1$ is preferably methyl.
$R_2$ is preferably alkyl.
$R_3$ is preferably the group $NR_4R_5$.
$R_4$ is preferably hydrogen.

When $R_5$ is alkanoyl or alkoxycarbonyl, this preferably contains 1 or 3 carbon atoms. When $R_5$ and/or $R_6$ contains a halogen atom, this is fluorine, chlorine or bromine, and especially chlorine or fluorine. When $R_5$ and/or $R_6$ contains more than one halogen substituent, then these substituents are preferably identical.

$R_5$ is preferably $SO_2R_6$.

When $R_6$ is mono-, di- or tri-halogenalkyl, this preferably contains 1 to 3 carbon atoms. When $R_6$ is monosubstituted phenyl, the substituent is preferably halogen and especially chlorine or fluorine.

$R_6$ is preferably alkyl, phenyl, mono-substituted phenyl, pyridyl or a group $NR_7R_8$.

When $R_7$ and/or $R_8$ is alkyl, this contains preferably 1 to 3 carbon atoms, especially 2 or 1 carbon atom. $R_7$ and $R_8$ are preferably identical. n is preferably 4 or 5.

A is preferably oxygen.

A preferred group of compounds includes compounds of formula I, wherein X is hydrogen. $R_1$ and $R_2$ are each methyl and $R_3$ is $NHSO_2R_6^I$, wherein $R_6^I$ is alkyl, phenyl, phenyl mono-substituted by halogen, pyridyl, di(alkyl)amino or morpholino.

The present invention comprises a process (a) for the production of a compound of formula Ia,

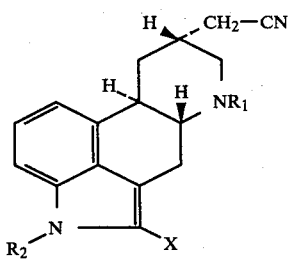

wherein X, $R_1$ and $R_2$ are defined above, replacing the group Z in a compound of formula II,

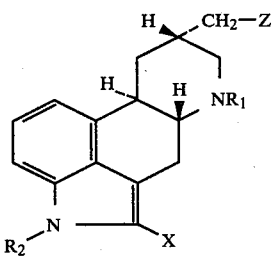

wherein.
Z is a leaving group, and
X, $R_1$ and $R_2$ are as defined above, by a cyano group, (b) for the production of a compound of formula Ib,

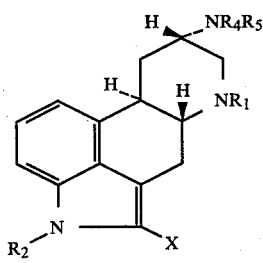

wherein X, $R_1$, $R_2$, $R_4$ and $R_5$ are as defined above,
reacting a compound of formula III,

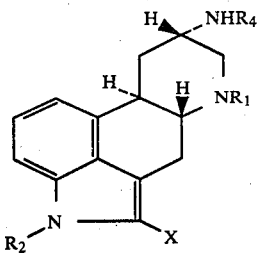

wherein X, $R_1$, $R_2$ and $R_4$ are as defined above, with a reactive functional derivative of a compound of formula $R_5OH$ wherein $R_5$ is as defined above, or
(c) for the production of a compound of formula Ic,

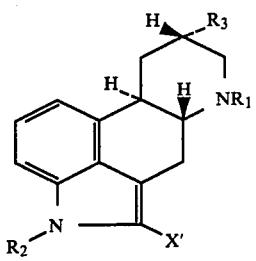

wherein
X' is chlorine or bromine, and
$R_1$, $R_2$ and $R_3$ are as defined above,
introducing a halogen atom into the 2-position of the ergoline nucleus of a compound of formula Id,

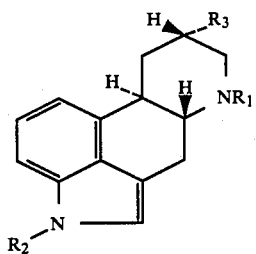

wherein X', $R_1$, $R_2$ and $R_3$ are as defined above.

Process (a) may be carried out in conventional manner for a nucleophilic substitution.

Z is preferably chlorine, bromine, or an aliphatic or aromatic sulphonyloxy radical, preferably mesyloxy or p-tosyloxy. As a suitable cyano group donar may be used an alkali metal cyanide such as sodium or potassium cyanide.

Suitable temperatures may be from 50° to 100° C.

Process (b) may be effected in conventional manner for a N-acylation. When $R_5$ is formyl, the reactive functional derivative is preferably the mixed acid anhydride of formic acid and acetic acid, otherwise the corresponding acid halide, e.g. the acid chloride or bromide may be used. Alternatively, when $R_5$ is alkanoyl of 2 to 5 carbon atoms, the corresponding symmetrical acid anhydride may be used.

The reaction is conveniently effected in a solvent, e.g. methylene chloride or dioxane. When an acid anhydride is used, an excess thereof may be used as solvent.

Suitable temperatures lie between $-10°$ C. and room temperature. When $R_5$ is formyl and when the mixed acid anhydride mentioned above is used, a slightly higher temperature, e.g. 40° to 60° C. may be used.

Preferably a tertiary base such as triethylamine, pyridine or 2,6-dimethylpyridine is present.

Process (c) may be effected in conventional manner for such halogenation reactions. Suitable halogenation agents include N—X'—succinimide or N—X'—phthalimide, wherein X' is as defined above. Suitable solvents are dioxane or chloroform. The reaction may be effected at from 10° to 100° C.

Free base forms of the compounds of formula I may be converted into acid addition salt form in conventional manner and vice versa. The hydrochloride is a suitable salt.

Insofar as the preparation of the starting materials is not particularly described, these may be produced in conventional manner or as described in the Examples.

In the following Examples all temperatures are in degrees Centigrade, and are uncorrected.

EXAMPLE 1

1,6-Dimethyl-8α-(N,N-dimethylsulfamoylamino)ergoline-(I)

2.55 g (10 millimol) of 1,6-dimethyl-8α-aminoergoline I are dissolved in 20 ml of 2,6-lutidine and are added dropwise within 10 minutes to a stirred mixture of 3.58 g (25 millimol) of N,N-dimethylsulfamic acid chloride, 40 ml of methylene chloride and 10 ml of 2,6-lutidine. Upon stirring for one hour at room temperature 1.5 ml of N,N-dimethylsulfamic acid chloride are added and stirring is effected for 2 hours at room temperature. Working up is effected by adding 2 N ammonia at 0° until basic and extraction is effected with a mixture of 10% methanol in methylene chloride. Upon drying over sodium sulphate, the organic phase is treated with active charcoal and is concentrated by evaporation at the rotary evaporator. The resulting, greenish foam is chromatographed on 150 g of silica gel, whereupon the title compound is eluted with 2% methanol in methylene chloride as yellowish resin. The hydrochloride of the title compound crystallizes from ethanol, M.P. 226°-228° $[\alpha]_D^{20} = -23°$ (c=0.3 in pyridine).

The 1,6-dimethyl-8α-amino-ergoline I required as starting compound is obtained by hydrogenation of 1-methyl-$\Delta^{7,8}$-lysergic acid methyl ester upon the addition of platinum oxide, reaction of the resulting 1-methyl-9,10-dihydro-isolysergic acid I-methyl ester (M.Pt. 150°-151°) with a mixture of hydrazine hydrate and hydrazine dihydrochloride and conversion of the resulting 1-methyl-9,10-dihydro-isolysergic acid I-hydrazide (M.Pt. 208°-211°) according to Curtius.

EXAMPLE 2

Analogous to Example 1 the following compounds are obtained:
(a) 1,6-dimethyl-8α-N-ethoxycarbonyl-N-methylaminoergoline I; M.Pt. 228°-230° (hydrochloride); $[\alpha]_D^{20} = -26°$ (c=0.3 in dimethylformamide).
(b) 1,6-dimethyl-8α-ethoxycarbonylamino-ergoline I; M.Pt. 300°-301° (hydrochloride) (decomp.); $[\alpha]_D^{20} = +43°$ (c=0.3 in dimethylformamide).
(c) 1,6-dimethyl-8α-(N,N-diethylsulfamoyl-amino)-ergoline I; M.Pt. 199°-201° (methanesulphonate); $[\alpha]_D^{20} = -25°$ (c=0.3 in dimethylformamide).

EXAMPLE 3

1,6-Dimethyl-2-bromo-8α-(N,N-dimethylsulfamoylamino)-ergoline I 1.5 g of 1,6-dimethyl-8α-(N,N-dimethylsulfamoylamino)-ergoline I are added to 125 ml of dioxane (absolute). 1.2 g of N-bromo-succinimide in 100 ml of dioxane are added dropwise while stirring and the resulting brown solution is stirred for another 2 hours at room temperature. The reaction mixture is concentrated by evaporation, dissolved in methylene chloride, treated with active charcoal and is worked up in the usual way. The residue is dried for 30 minutes in a high vacuum at 60°. The hydrochloride of the title compound (from ethanol) has a M.Pt. of 252°–254° (decomposition). The optical rotation amounts to $[\alpha]_D^{20} = +10°$ (c=1 in dimethyl formamide).

Following Example 3, the following compounds of formula I may also be produced, wherein X is H, $R_1$ is $C_2H_5$, $R_2$ is $CH_2=CH-CH_2$, and $R_3$ is:

| | |
|---|---|
| $CH_2CN$ | (i) |
| $N(nBu)COO^nBu$ | (ii) |
| $N(nBu)COOCH_2.CHCl.CH_3$ | (iii) |
| $N(nBu)SO_2^nBu$ | (iv) |
| $N(nBu)SO_2CHCl_2.^nC_3H_7$ | (v) |
| $N(nBu)SO_2CH_2Cl.CH_3$ | (vi) |
| $N(nBu)SO_2CH_2CCl_3$ | (vii) |
| $N(nBu)SO_2C_6H_5$ | (viii) |

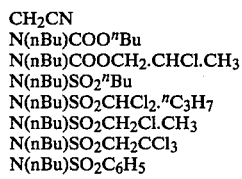 (ix)

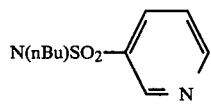 (x)

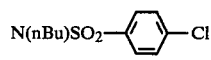 (xi)

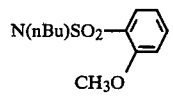 (xii)

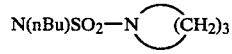 (xiii)

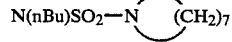 (xiv)

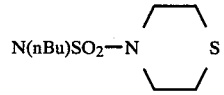 (xv)

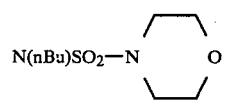 (xvi)

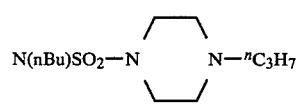 (xvii)

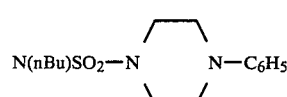

The compounds of formula I are useful as prolactin secretion inhibiting agents, e.g. for the treatment of galactorrhoa, prostrate hypertrophy and prostrate or mamma carcinoma as indicated in standard tests, e.g. an inhibition of ovum implantation on female rats on the fifth day after insemination on administration s.c. of a dose of from 0.01 to about 5 mg/kg animal body weight of the compounds. The test may be carried out as follows:

The compound under investigation is administered to female rats 5 days after coitus and shown to be sperm positive according to the vaginal smear test. The rats are sacrificed on day 12 and their uteri are examined by means of the Salewski reaction for proof that the nidation process has been interrupted [Arch. exp. Path. Pharm. 247, 367 (1967)].

For this use the dosage will, of course, vary depending on the compound employed, mode of administration and treatment desired. However, in general, satisfactory results are obtained when administered at a daily dosage of from about 0.005 mg to about 5 mg per kg animal body weight, conveniently given in divided doses 2 to 4 times a day or in sustained release form. For the larger mammals, the total daily dosage is in the range from about 0.05 to about 50 mg, and dosage forms suitable for oral administration comprise from about 0.01 mg to about 25 mg of the compounds admixed with a solid or liquid pharmaceutical carrier or diluent.

The compounds of formula I, wherein $R_3$ is $-NHSO_2N(CH_3)_2$, especially the Example 1 compound, exhibit particularly interesting activity in this test.

The compounds of formula I are furthermore useful as central dopaminergic stimulant agents, for example, for treating Morbus Parkinson, as indicated by standard tests, for example according to the principles of U. Ungerstedt Acta Physiol. Scand. Suppl. (1971) 367, 69–93, by an induction of contralateral turning in rats lesioned unilaterally in the substantia nigra by 6-hydroxydopamine an i.p. administration of from about 0.3 to about 5 mg/kg animal body weight and by an induction of dose dependent stereotyped sniffing, licking and biting behaviour in the rat according to the following test:

Rats, 180–222 g, are placed in perspex cylinders of 30 cm diameter on a wire grid floor. After 30 minutes to allow acclimatisation to the cage, the rats are injected with the compound under investigation. The behaviour of the rats is observed for 2 minutes at 30 minute intervals for 2 hours and then at 60 minute intervals for a total of up to 7 hours. The degree of stereotyped behaviour observed is assessed using a scoring system based on that described by Costall, Naylor and Olley [Euro J. Pharmac. 18, 83–94 (1972)].

The score and criteria are as follows:
1. Intermittent sniffing
2. Persistent sniffing, occasional licking
3. Licking, occasional biting
4. Intense and persistent biting.

In this test the compounds are administered i.p. at from 1 to 40 mg/kg animal body weight.

For the above mentioned use the dosage will, of course, vary depending on the compound employed, mode of administration and therapy desired. However, in general, satisfactory results are obtained when administered at a daily dosage of from 0.005 mg to about 50 mg per kg animal body weight, conveniently given in divided doses 2 to 4 times a day or in sustained release form. For the larger mammals, the total daily dosage is in the range from about 10 to about 200 mg, and dosage forms suitable for oral administration comprise from about 2 mg to about 100 mg of the compounds admixed with a solid or liquid pharmaceutical carrier or diluent.

The compounds of formula I are furthermore useful as anti-depressant agents, as indicated in standard tests, e.g. by an inhibition of the tetrabenazine-induced catalepsy in rats on i.p. administration of from 1 to 50 mg/kg of the compounds.

For this use the dosage will, of course, vary depending on the compound employed, mode of administration and treatment desired. However, in general, satisfactory results are obtained when administered at a daily dosage of from about 0.05 mg to about 50 mg per kg animal body weight, conveniently given in divided doses 2 to 4 times a day or in sustained release form. For the larger mammals, the total daily dosage is in the range from about 5 to about 20 mg, and dosage forms suitable for oral administration comprise from about 1 mg to about 10 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be formulated in conventional manner, so as to be, for example, a solution or a tablet.

In a group of compounds $R_1$ is methyl; $R_2$ is alkyl and $R_3$ is $-NHSO_2NR_7{}^I R_8{}^I$, wherein $R_7{}^I$ and $R_8{}^I$ are, independently, alkyl of 1 to 4 carbon atoms.

We claim:

1. A compound of formula I,

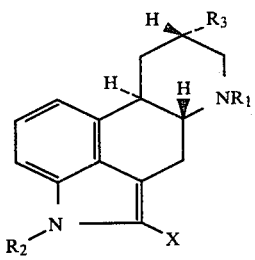

wherein

X is hydrogen, chlorine or bromine,
$R_1$ is methyl or ethyl,
$R_2$ is alkyl of 1 to 4 carbon atoms or allyl,
$R_3$ is a group $-NR_4R_5$, wherein $R_4$ is hydrogen or alkyl of 1 to 4 carbon atoms, and $R_5$ is $SO_2R_6$, wherein $R_6$ is alkyl of 1 to 4 carbon atoms, mono-, di- or tri-haloalkyl of 1 to 4 carbon atoms, phenyl, phenyl mono-substituted by halogen or alkoxy of 1 to 4 carbon atoms, or pyridyl, or $R_6$ is a group $NR_7R_8$, wherein $R_7$ and $R_8$ are, independently, hydrogen or alkyl of 1 to 4 carbon atoms, or $R_7$ and $R_8$ together form $-[CH_2]_n-$ or $-[CH_2]_2-A-[CH_2]_2-$, wherein n is a whole number from 3 to 7, and A is oxygen, sulphur, or nitrogen substituted by alkyl of 1 to 4 carbon atoms or phenyl, in free base form or in pharmaceutically acceptable acid addition salt form.

2. A method of inhibiting lactation in animals, treating Morbus Parkinson or treating depressions in animals which comprises administering a therapeutically effective amount of a compound of claim 1 to an animal in need of such treatment.

3. A pharmaceutical composition useful in inhibiting lactation, treating Morbus Parkinson or treating depression which comprises a therapeutically effective amount of a compound of claim 1 in association with a pharmaceutical carrier or diluent.

4. A compound according to claim 1 in which X is hydrogen.

5. A compound according to claim 1 in which $R_1$ is methyl.

6. A compound according to claim 1 in which $R_2$ is alkyl.

7. A compound according to claim 1 in which $R_4$ is hydrogen.

8. The compound according to claim 1 which is 1,6-dimethyl-8α-(N,N-dimethylsulfamoylamino)ergoline-I.

9. The compound according to claim 1 which is 1,6-dimethyl-8α-(N,N-diethylsulfamoylamino)ergoline-I.

10. The compound according to claim 1 which is 1,6-dimethyl-2-bromo-8α-(N,N-dimethylsulfamoylamino)ergoline-I.

11. A pharmaceutical composition according to claim 3 in which the compound is 1,6-dimethyl-8α-(N,N-dimethylsulfamoylamino)ergoline-I.

12. A method according to claim 2 in which the compound is 1,6-dimethyl-8α-(N,N-dimethylsulfamoylamino)ergoline-I.

* * * * *